United States Patent
Müller et al.

(10) Patent No.: US 11,510,846 B2
(45) Date of Patent: Nov. 29, 2022

(54) SENSOR DEVICE FOR ASSISTING AN AIDER WITH A CARDIOPULMONARY RESUSCITATION

(71) Applicants: Michael Müller, Freiburg (DE); Matthias Roth, Freiburg (DE); Per Schorling, Svendborg (DK)

(72) Inventors: Michael Müller, Freiburg (DE); Matthias Roth, Freiburg (DE); Per Schorling, Svendborg (DK)

( * ) Notice: Subject to any disclaimer, the term of this patent is extended or adjusted under 35 U.S.C. 154(b) by 294 days.

(21) Appl. No.: 16/631,841

(22) PCT Filed: Jul. 18, 2018

(86) PCT No.: PCT/DE2018/100656
§ 371 (c)(1),
(2) Date: Jan. 17, 2020

(87) PCT Pub. No.: WO2019/015727
PCT Pub. Date: Feb. 24, 2019

(65) Prior Publication Data
US 2020/0155412 A1 May 21, 2020

(30) Foreign Application Priority Data

Jul. 20, 2017 (DE) .......................... 102017116361.1

(51) Int. Cl.
*A61H 31/00* (2006.01)
(52) U.S. Cl.
CPC ..... *A61H 31/005* (2013.01); *A61H 2031/002* (2013.01); *A61H 2201/5015* (2013.01);
(Continued)
(58) Field of Classification Search
CPC .................. A61H 31/00; A61H 31/005; A61H 2031/002; A61H 2201/5061; A61H 2201/5084; A61H 2201/5097
See application file for complete search history.

(56) References Cited

U.S. PATENT DOCUMENTS 5,619,804 A * 4/1997 Vogt ..................... G01B 3/1084
33/759
6,782,293 B2 * 8/2004 Dupelle ................. A61N 1/046
607/152

(Continued)

FOREIGN PATENT DOCUMENTS

CH        710687 A2     8/2016
DE   602004002147 T2   12/2004

(Continued)

OTHER PUBLICATIONS

Wintape Measuring Tape Company, 2012, https://www.tapemeasuring.com/body-tape-measure/body-measuring-tape/body-fitness-tape-measure.html). (Year: 2012).*

(Continued)

*Primary Examiner* — Samchuan C Yao
*Assistant Examiner* — Sarah B Lederer
(74) *Attorney, Agent, or Firm* — Michael Soderman

(57) ABSTRACT

The invention relates to a sensor device for capturing data when carrying out first aid measures for reanimating a person affected by a cardiac arrest. The sensor device is exactly positioned on the chest of the patient by means of a positioning-aid apparatus (5) and affixed by means of a fastening means (2). The thorax compressions, i.e., the pressing-in depth and compression frequency, are detectable by means of a motion sensor. A data-transfer interface allows communication, e.g. wireless communication, with a mobile terminal.

9 Claims, 1 Drawing Sheet

(52) U.S. Cl.
CPC ............... *A61H 2201/5061* (2013.01); *A61H 2201/5084* (2013.01); *A61H 2201/5097* (2013.01)

(56) References Cited

U.S. PATENT DOCUMENTS

| | | | |
|---|---|---|---|
| 8,034,006 B2* | 10/2011 | Celik-Butler | G09B 23/288 600/587 |
| 2002/0177793 A1* | 11/2002 | Sherman | A61H 31/005 601/41 |
| 2006/0270952 A1* | 11/2006 | Freeman | A61H 31/005 601/41 |
| 2008/0171311 A1* | 7/2008 | Centen | G09B 23/288 601/41 |
| 2008/0300518 A1* | 12/2008 | Bowes | A61H 31/005 601/41 |
| 2014/0135666 A1* | 5/2014 | Butler | A61H 31/007 601/41 |
| 2015/0164417 A1* | 6/2015 | Tupin, Jr. | A61B 5/4848 600/407 |
| 2015/0182009 A1* | 7/2015 | Whang | A45F 5/00 224/222 |
| 2016/0361227 A1* | 12/2016 | Freeman | A61B 5/14551 |

FOREIGN PATENT DOCUMENTS

| | | |
|---|---|---|
| DE | 112010000978 T5 | 9/2010 |
| EP | 1128795 B1 | 11/1999 |
| EP | 1858472 B1 | 8/2006 |
| EP | 2255845 A1 | 12/2010 |
| KR | 20130122822 A | 11/2013 |
| WO | 2004037154 A2 | 5/2004 |
| WO | 2006104977 A2 | 10/2006 |
| WO | 2013093757 A1 | 6/2013 |
| WO | 2015110118 A1 | 7/2015 |
| WO | 2015189275 A1 | 12/2015 |
| WO | WO-2015189275 A1 * | 12/2015 ........... A61H 31/005 |

OTHER PUBLICATIONS

Koo HR, Lee YJ, Gi S, Khang S, Lee JH, Lee JH, Lim MG, Park HJ, Lee JW. The effect of textile-based inductive coil sensor positions for heart rate monitoring. J Med Syst. Feb. 2014;38(2):2. doi: 10.1007/s10916-013-0002-0. Epub Jan. 31, 2014. PMID: 24481717 (Year: 2014).*

* cited by examiner

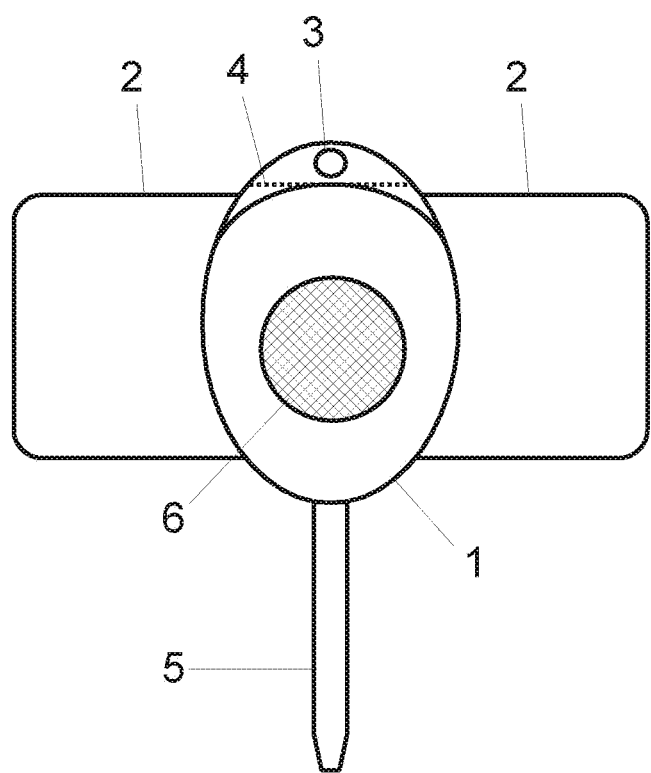

SENSOR DEVICE FOR ASSISTING AN AIDER WITH A CARDIOPULMONARY RESUSCITATION

CROSS REFERENCE TO RELATED APPLICATIONS

This application is the U.S. national stage of International Application No. PCT/DE2018/100656, filed on 2018 Jul. 18. The international application claims the priority of DE 102017116361.1 filed on 2017 Jul. 20; all applications are incorporated by reference herein in their entirety.

BACKGROUND

The invention relates to a sensor device for capturing data when carrying out first aid measures for reanimating a person affected by a cardiac arrest. The sensor device is connected to a display and feedback device, which is configured to guide on basis of a difference between performed cardiopulmonary resuscitation and recommended cardiopulmonary resuscitation, or applicable in combination with a defibrillator for resuscitation of a patient affected by a cardiac arrest, particularly by a lay rescuer in case of an emergency or during training of a cardiopulmonary resuscitation.

Sudden cardiac death is a leading cause of death. Despite considerable efforts in recent decades and the establishment of international guidelines for the treatment of cardiovascular arrest the survival rate stays below 10%. For example, 50.000 people are suffering from a cardiac arrest every year in Germany, of which the majority dies or survives only with permanent neurological damage.

Survival after sudden cardiac death is only possible if chest compressions are started within the first few minutes and before arrival of the emergency services.

These chest compressions should be performed according to the currently valid recommendations given by the guidelines. At present, the recommendation gives a compression depth of 5-6 cm and a compression frequency of approximately 100/min as well as a complete relief after each chest compression. Any interruptions of chest compressions—for example in order to ventilate or trigger a defibrillation shock—should be as short as possible so that the brain continuously is supplied with blood and no irreversible damage occurs.

In Germany, for instance, lay rescuers initiate the important measures of resuscitation (particularly chest compressions) in only about 40% of emergency situations. The quality of chest compressions after training on their basics is good, but deteriorates after six months again considerably. Furthermore, the quality of chest compressions during performing CPR (CPR—cardiopulmonary resuscitation) deteriorates considerably already after two minutes.

The probability of survival of a patient affected by a cardiac arrest depends essentially on the actions performed by the lay helper, who, however, is often overwhelmed by the situation and lacks appropriate training.

EP 1 128 795 B1 discloses a system for measuring and prompting breast-compressions. It includes a mobile CPR compression monitor for monitoring the chest compressions during resuscitation of a person affected by a cardiac arrest. The device is placed on the hand of the first aider or the patient and comprises acceleration sensors and an interface for data transmission. An evaluation unit with monitor is connected to this interface via a cable. This evaluation unit with monitor can be integrated in the CPR compression monitor or be a stand-alone device. This system is designed for trained and experienced medical staff.

WO 2006/104977 A2, EP 2 255 845 A1 and DE 60 2004 002 147 T2 disclose a professional medical system to support a first aider, who must be trained in resuscitation. The system includes, among other things, a defibrillator and a mobile display and control unit.

Similarly, EP 1 858 472 B1 describes a mobile, but complex medical system for assisting a helper during resuscitation, which also includes a defibrillator. It is intended to deploy the device at a few central locations with high numbers of people congregating, so first aiders can get a quick access to it. However, this device too can be used reasonably only by trained aiders.

Methods and apparatuses for accurately determining the depth of compressions during chest compressions are shown in WO 2004/037 154 A2 and DE 11 2010 000 978 T5.

Significant disadvantages of the known prior art solutions are that an application of appropriate help measures is time consuming and the respective first aider often is overburdened and insufficiently trained. In addition, a high level of knowledge is required to be capable of carrying out a successful emergency treatment of the patient.

WO 2015/110118 describes a system for assisting a first aider in the re-animation of a person affected by a cardiac arrest, which comprises a sticking plaster with a position sensor attached to it, wherein the position sensor transmits the compression depth and the massage frequency to a smartphone being in communication connection with the position sensor.

SUMMARY

The invention relates to a sensor device for capturing data when carrying out first aid measures for reanimating a person affected by a cardiac arrest. The sensor device is exactly positioned on the chest of the patient by means of a positioning-aid apparatus (5) and affixed by means of a fastening means (2). The thorax compressions, i.e., the pressing-in depth and compression frequency, are detectable by means of a motion sensor. A data-transfer interface allows communication, e.g wireless communication, with a mobile terminal.

DETAILED DESCRIPTION

The objective of the present invention is to provide a sensor device for capturing data when carrying out first aid measures for reanimating a person affected by a cardiac arrest, in the following called patient, that enables an untrained lay rescuer to immediately perform guided first lifesaving measures, wherein the sensor device should be small and compact enough to be carried along at all times, and wherein the sensor device should be absolutely intuitive in its handling so that it can be used for resuscitation even in stressful situations and without previous medical knowledge.

The objective is achieved according to the invention by a sensor device with the features according to the patent claim 1; advantageous implementations of the invention are described in the dependent claims.

According to the invention, a sensor device for capturing relevant data when performing a cardiac massage for reanimating a person affected by a cardiac arrest is provided which therefore allows for supporting a first aider, who especially is an untrained lay in resuscitation, during resuscitation of patients suffering from a cardiac arrest.

The sensor device comprises a largely rigid, preferably at least partially rigid, flat housing body which is watertight. For example, the housing body may be shaped like a lentil or a shell. In particular, the housing body may have—at least in some areas—an elasticity which allows it to be adapted to the shape of the aider's hand or the patient's chest when conducting a cardiac massage, e.g. with an applied force of about 800 N. Thus, the pressure can be equalized and damage to the skin may be prevented.

Within the housing body at least a motion sensor, a storage for electrical energy, a processor and an interface for sending and/or receiving data and/or commands are arranged.

The interface may be wireless, wherein preferably it is configured to send and receive, respectively, electromagnetic waves according to e. g. a Bluetooth-, NFC- or WLAN-standard.

The sensor device furthermore comprises at least one fastening means for fixing the device on the breast of a patient as well as a positioning-aid apparatus for an exact positioning of the housing body on the breast.

On the outside of the housing, the same has an adhesive surface in the form of an adhesive coating on at least one area of the surface which—when the sensor device is used as intended during resuscitation—comes into contact, for example, with the hand of the first aider pressing on the patient's chest by means of the sensor device. Thus, through the indirect connection of the hand with the chest—in combination with the shape of the housing—a suction effect is generated during the second movement phase of the heart pressure massage, whereby an active relief of the chest is made possible.

The sensor device may be a pendant, preferably a keyring pendant to be fastened e. g. to a bunch of keys. The dimensions of the sensor device when being transported preferably are less than 10 cm×10 cm×2 cm.

The processor is configured to evaluate the data captured by the at least one sensor and to convert said data into a form which can be displayed and/or computed further by a mobile terminal device being in a communication connection to the processor via the interface of the sensor device. Said mobile terminal device being in a communication connection to the sensor device may be any type of stand-alone portable monitor, industrial display, small computer or microcomputer, such as a smartwatch, smartphone, phablet, tablet or netbook.

The advantage of the sensor device lies in the fact that, due to its design, particularly its small dimensions, it always (i.e. at any time) can be carried along by practically any person willing to help. The sensor device can be used instanter in case a compatible mobile terminal device is available, i.e. lengthy preparations or waiting for medically trained aiders can be prevented.

Additionally, the sensor device may comprise an activation device, e. g. a switch or a tab by means of which the electronic or electrical components in the housing, e.g. the processor, can be connected to the storage for electrical energy.

The fastening means of the sensor device preferably is a medical type adhesive tape, e. g. a sticking-plaster. Here, on each of the two opposite long sides of the housing body of the sensor device—e.g. like wings—an adhesive plaster can be fastened or may be pulled out, wherein in the storage or transport state of the sensor device said adhesive plasters are folded down onto the outside of the housing body of the sensor device or stowed in the housing body.

According to an alternative embodiment the fastening means may be a hook-and-loop fastener or part of a hook-and-loop fastener exhibiting barbs or loops.

The storage for electrical energy may be a disposable battery or a rechargeable battery cell, wherein charging of the storage for electrical energy may be performed inductive, i. e. the sensor device in this case additionally comprises an inductively working charging interface to be coupled to an inductively working charging device.

Prior to using the sensor device it may be required to activate it by using its activation device, e. g. by bending or breaking a part of the housing body or a tab at a predetermined breaking point, or by pulling a tab, e.g. designed as an insulator, out of the housing body or by pulling the fastening means in the form of an adhesive plaster out of the housing body. It may be provided, too, to couple the activation device to the positioning-aid apparatus in that actuating the positioning-aid apparatus in order to position the sensor device exactly on the patient's chest establishes the power supply.

Alternatively or additionally the activation device may comprise a switch arranged within the housing body, said switch comprising a pressure or force sensor. As soon as the first aider is pressing onto the chest of the patient using the sensor device, said switch activates the sensor device. In particular, the switch may be configured to trigger upon exceeding a preset pressing force, e. g. 800 N.

According to an embodiment the motion sensor is an acceleration sensor, preferably a three-axis acceleration sensor, wherein pressing-in depth as well as compression frequency may be calculated from the data gathered by the sensor. Additionally it may be provided that the sensor device comprises two, particularly redundant, motion sensors.

The sensor device may comprise additional sensors like e. g. a force sensor.

The positioning-aid apparatus attached to or integrated into the housing body can be in the form of a measuring standard, e.g. a tape, cord or rod of a given length, which can be folded out or pulled out of the housing. Preferably the positioning-aid apparatus is a flexible, e. g. rollable, measuring standard which can be pulled out, wherein its maximum length is 8 cm, preferably 5 cm.

It may be provided that the measuring standard exhibits mark positions—e. g. designed as snap-in points, each of which defines a specified pull-out length of the measuring standard when it is pulled out of the housing body—for patients of different body sizes, for example a mark for infants, a mark for teenagers and one for adult men or women. Thus, by arranging the measuring standard at the sternum, an exact placement of the sensor device on the chest of the patient is possible.

In particular the invention may be designed such that the measuring standard consists of a flexible or rigid fibre-reinforced plastic, e.g. carbon-fibre-reinforced plastic (CFRP) or aramide, the temperature-dependent coefficient of linear expansion of which may be substantially zero.

According to an embodiment the measuring standard may be electrical conductive or comprise an electric conductor, wherein it is connected to the wireless interface. In this way, the measuring standard advantageously can be used as an antenna for sending and/or receiving of data and/or commands via the wireless interface.

Alternatively or additionally it may be provided that the measuring standard exhibits at one of its sides an at least partially applied adhesive layer in that the measuring standard is fixable on the chest of the patient when using the positioning-aid apparatus.

The sensor device further may be designed to comprise an inductively working sensor to detect electric currents running through the patient's chest. By usage of said sensor a defibrillation shock may be identified.

According to an embodiment the adhesive coating applied to the surface area of the housing body which comes into contact with the hand of the aider during the intended use of the sensor device can be a gel or silicone. Here, it may be provided that the adhesive coating is covered by a protective cover, which e. g. needs to be removed during activating or in order to activate the sensor device.

Furthermore, the sensor device may comprise an acoustic and/or haptic feedback device which, for example, by means of vibrating is signaling a deviation and/or a correspondence between the cardiopulmonary resuscitation performed and the recommended cardiopulmonary resuscitation. Said feedback device may be controlled by an external mobile terminal device to be connected to the interface of the sensor device. Alternatively or additionally the feedback device may be driven by the processor of the sensor device.

In order to use it, the sensor device is affixed to the sternum of a patient or a training manikin by means of the fastening means, in that the aider is pressing on the chest via the sensor device. The sensor device is thus moved along with the movements of the sternum during a cardiac pressure massage, i.e. thoracic compressions. When performing thoracic compressions, the associated compression movements can be detected by the sensors.

The sensor device is to be connected to a mobile terminal device by means of its interface. In particular, the mobile terminal device may be configured to receive the data collected by means of the sensor device for determining the depth of compression (by which the breast is pressed-in during thoracic compression) and/or the frequency of the thoracic compressions and to guide the first aider on basis of these determined values.

BRIEF DESCRIPTION OF THE DRAWINGS

FIG. 1 shows a sensor device in the form of a key fob.

DETAILED DESCRIPTION OF THE PREFERRED EMBODIMENTS

The invention is explained in more detail below with the aid of an exemplary embodiment with reference to the FIGURE, the same or similar features being provided with the same reference numerals; schematically shown in the FIGURE is a plan view of the sensor device.

The sensor device in the form of a key fob comprises the rigid, flat housing body 1 and the fastening means 2 in the form of two flexible plaster stripes affixed at each side of the housing body 1, said plaster stripes being folded onto the housing body 1 in the transport state of the key fob. The hanger 3 is used for fastening the sensor device to a key ring. The adhesive coating 6 is applied to the housing body 1.

In order to activate the sensor device the hanger 3 is to be bent at the predetermined breaking point 4. By doing so a wireless communication connection via the Bluetooth interface (not depicted) to a smartphone (not depicted) is established in that data collected by the sensor device can be transferred to said smartphone.

After it has been pulled out of the housing body 1, the positioning-aid apparatus 5 is placed with its tip on the lower part of the sternum, whereby the sensor device comes to lie exactly in the medically correct position on the patient's chest.

LIST OF REFERENCE NUMERALS

1 housing body
2 fastening means
3 hanger
4 predetermined breaking point
5 positioning-aid apparatus
6 adhesive coating

The invention claimed is:

1. A sensor device for assisting an aider with a cardiopulmonary resuscitation of a patient affected by a cardiac arrest, comprising a fastener for fastening the sensor device to the chest of a patient, a motion sensor and an interface for sending and/or receiving of data and/or commands, characterized in that the sensor device is a pendant of dimensions less than 10 cm×10 cm×2 cm, wherein the sensor device furthermore comprises:
   a largely flat and watertight housing body which is enclosing the motion sensor, a storage for electrical energy, a processor and the interface, wherein the housing body comprises an upper side, which is contacting a hand of the aider during the intended use of the sensor device, and a lower side which is contacting the chest of the patient during the intended use of the sensor device;
   an auxiliary positioner for exactly positioning the sensor device on the chest of the patient wherein the auxiliary positioner is a measuring standard which can be pulled out of the housing body;
   an activation device for connecting at least the processor to the storage for electrical energy, wherein the activation device is part of the auxiliary positioner; and
   an adhesive coating at least on a surface region of the upper side of the housing body wherein the adhesive coating is silicone.

2. A sensor device according to claim 1, characterized in that the interface is wireless.

3. A sensor device according to claim 1, characterized in that the storage for electrical energy is rechargeable, wherein the sensor device comprises an inductive charging interface for an inductive charging device.

4. A sensor device according to claim 1, characterized in that the motion sensor is an acceleration sensor.

5. A sensor device according to claim 1, characterized in that it comprises a hook and loop fastener on the region of the housing wall which comes into contact with the chest.

6. A sensor device according to claim 1, characterized in that the measuring standard consists of fibre-reinforced plastic.

7. A sensor device according to claim 1, characterized in that it comprises an inductive sensor for detecting electric currents running through the chest of the patient.

8. A sensor device according to claim 1, characterized in that the fastener is in the form of two flexible adhesive strips which are arranged laterally and opposite one another on the housing body and can be pulled out of the housing body or folded away from the housing body for fastening the sensor device.

9. The sensor device according to claim 2, characterized in that the measuring standard is electrically conductive or comprises an electric conductor, wherein said measuring standard is connected to the wireless interface in that the measuring standard is used as an antenna for sending and/or receiving data and/or commands via the wireless interface.

\* \* \* \* \*